(12) United States Patent
Neil et al.

(10) Patent No.: US 8,334,899 B1
(45) Date of Patent: Dec. 18, 2012

(54) PROTECTIVE LASER BEAM VIEWING DEVICE

(75) Inventors: George R. Neil, Williamsburg, VA (US); Kevin Carl Jordan, Newport News, VA (US)

(73) Assignee: Jefferson Science Associates, LLC, Newport News, VA (US)

( * ) Notice: Subject to any disclaimer, the term of this patent is extended or adjusted under 35 U.S.C. 154(b) by 420 days.

(21) Appl. No.: 11/982,128

(22) Filed: Nov. 1, 2007

(51) Int. Cl.
*A62B 1/04* (2006.01)
*H04N 7/00* (2011.01)
*H04N 7/18* (2006.01)
*G09G 5/00* (2006.01)

(52) U.S. Cl. ............................ 348/67; 348/115; 345/7

(58) Field of Classification Search ............. 348/67, 348/115; 345/7, 8, 9
See application file for complete search history.

(56) References Cited

U.S. PATENT DOCUMENTS

| | | | |
|---|---|---|---|
| 5,760,852 A * | 6/1998 | Wu et al. | 349/14 |
| 5,864,481 A * | 1/1999 | Gross et al. | 700/90 |
| 6,281,927 B1 * | 8/2001 | Otto et al. | 348/61 |
| 6,396,463 B1 * | 5/2002 | Tomono | 345/8 |
| 6,556,336 B2 * | 4/2003 | Hutcheson et al. | 359/241 |
| 7,202,852 B2 * | 4/2007 | Harvie | 345/158 |
| 2004/0119662 A1 * | 6/2004 | Dempski | 345/8 |
| 2007/0046776 A1 * | 3/2007 | Yamaguchi et al. | 348/53 |
| 2009/0231417 A1 * | 9/2009 | Demonchy | 348/53 |

* cited by examiner

*Primary Examiner* — Kelly L Jerabek

(57) ABSTRACT

A protective laser beam viewing system or device including a camera selectively sensitive to laser light wavelengths and a viewing screen receiving images from the laser sensitive camera. According to a preferred embodiment of the invention, the camera is worn on the head of the user or incorporated into a goggle-type viewing display so that it is always aimed at the area of viewing interest to the user and the viewing screen is incorporated into a video display worn as goggles over the eyes of the user.

4 Claims, 1 Drawing Sheet

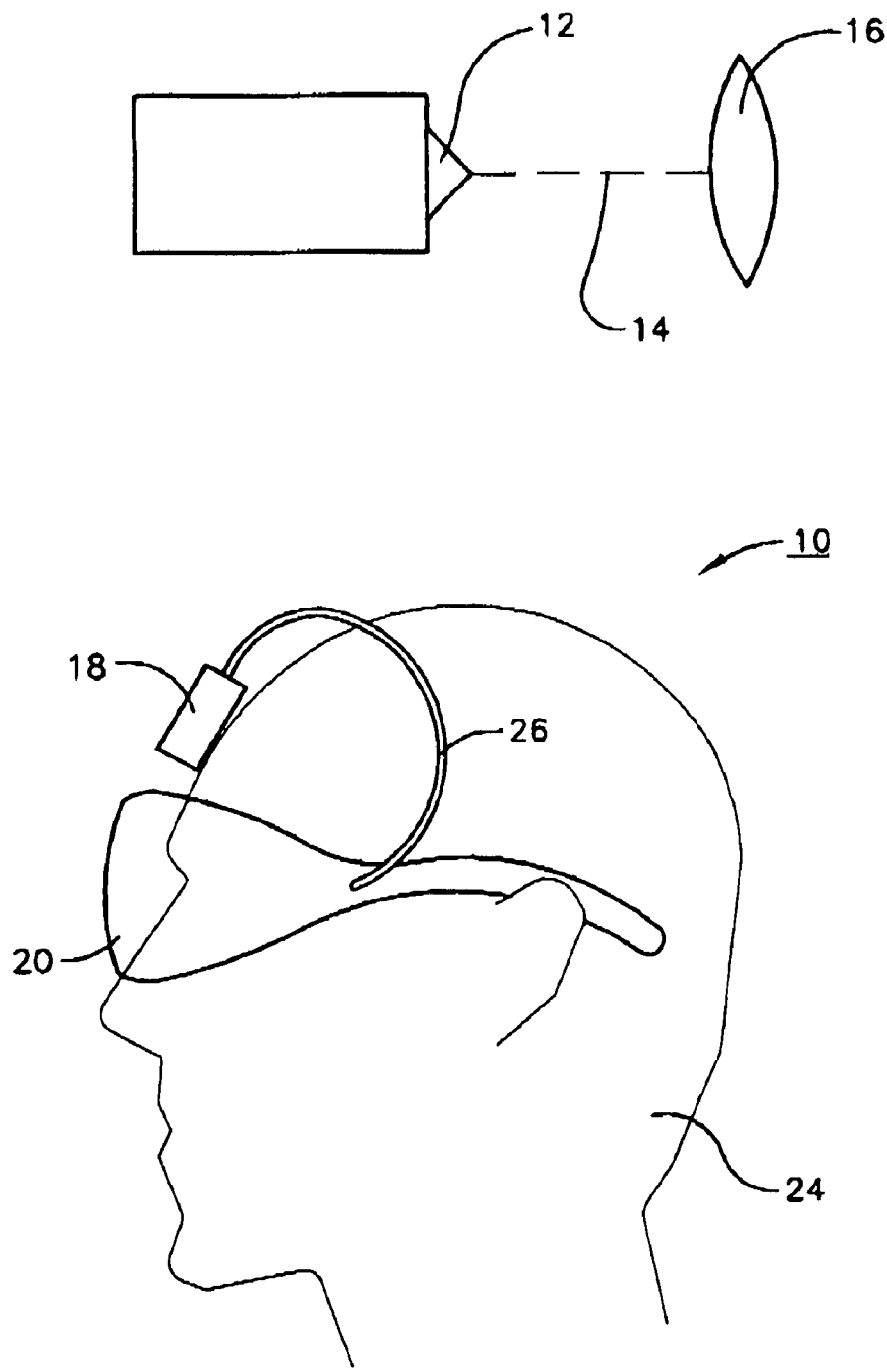

PROTECTIVE LASER BEAM VIEWING DEVICE

The United States of America may have certain rights to this invention under Management and Operating Contract DE-AC05-06OR23177 from the United States Department of Energy.

FIELD OF THE INVENTION

The present invention relates to devices for viewing laser beams and more particularly to such a device that provides increased safety for the user of such devices by isolating the user from any exposure to the actual path of the laser beam.

BACKGROUND OF THE INVENTION

High power lasers in use today produce intensities that can cause severe eye damage or even blindness. As a consequence, users of such lasers are required to wear eye protection in the form of protective goggles. Standard protective goggles for such use are typically made of materials which absorb at the wavelength of the laser light but permit other wavelengths of light to pass so that the user can observe his surroundings and perform work in a relatively normal manner. While such goggles are effective in protecting those exposed to stray laser radiation, they do have a number of practical limitations. First, they must be designed for a particular wavelength or wavelength band. They can only be used with the laser for which they were designed. If other lasers are present with outputs outside of the design wavelength band, then a combination of filtering is required or a potential use hazard exists. Secondly, in order to be safe, the lenses must filter out such high levels of laser light that it becomes difficult or impossible to view where the laser beam is directed. This leads many users to adopt unsafe practices such as looking around the edges of the eyewear when aligning the beam, a very dangerous practice.

OBJECT OF THE INVENTION

It is therefore an object of the present invention to provide a laser viewing device or system that provides for only indirect viewing of laser beams, thus eliminating any possibility of direct exposure of the eye of the user to the laser beam, all while providing adequate viewing capability so that the user is not tempted to subvert the use of the protective device.

SUMMARY OF THE INVENTION

According to the present invention, there is provided a laser viewing system or device comprising a camera selectively sensitive to laser light wavelengths and a viewing screen receiving images from the laser sensitive camera. According to a preferred embodiment of the invention, the camera is worn on the head of the user so that it is always aimed at the area of viewing interest to the user and the viewing screen is incorporated into a video display worn as goggles over the eyes of the user.

DESCRIPTION OF THE DRAWINGS

FIG. 1 is a schematic depiction of the protective laser viewing device of the present invention in use on the head of a user.

DETAILED DESCRIPTION

The protective viewing system of the present invention utilizes a video camera sensitive to the wavelength of the laser being observed connected to one or more video displays worn in front of the eyes. All direct laser radiation is stopped by the goggle like video viewer(s) and only that displayed on the video displays before the eyes of the user is shown to the user. This system thus provides a method for viewing the laser beam without any danger of damaging the eyes of the user. Using the viewing device of the present invention it also becomes possible using appropriate camera technology, i.e. specific laser light wavelength sensitive camera technology, to safely view the actual laser beam rather than a manifestation thereof generated by the presence of mist or other particulate in the beam path for alignment purposes. Such alignment can be accomplished even if the laser beam is invisible to the naked eye. Finally, the protective laser viewing system of the present invention regardless of the laser in use so that the presence of multiple laser wavelengths from various neighboring lasers that might be in use simultaneously poses no additional threat to the eyes of the user.

Referring now to the accompanying drawings, as shown in FIG. 1, the protective laser viewing device of the present invention 10 comprises a laser 12, producing a laser beam 14 aimed at a target 16, a laser wavelength band sensitive camera 18 viewing laser beam 14 and a viewing device in the form of goggles 22 worn on the head 24 of a user.

Laser wavelength band sensitive camera 18 can be attached, i.e. form part of the goggle assembly 22, or be worn on the user's head as depicted schematically in FIG. 1 to permit the user to observe that which would normally be viewed without the camera and goggle arrangement described herein. In the case where the camera is attached to the user head 24, a suitable strap or other mechanism can be used to maintain the position of camera 18 on the head of the user while a cable or other connective device 26 can be used to transmit images captured by camera 18 for projection onto goggles 22.

As an alternative embodiment, a pair of cameras transmitting parallel images to displays in goggles 22 could be used to provide a stereoscopic images or images in multiple wavelength regions side by side or overlaid.

As used herein, the term "goggles" is meant to define and include any visual arrangement that places the laser beam image immediately before the eye of a user such as conventional goggles or display screens that are suspended in one fashion or another immediately in front of or to one side of the eye, thereby providing an image of what is being viewed by camera 18 to the user. As will be apparent to the skilled artisan, goggles may include single or monocular image displays or more conventional binocular image displays.

As the invention has been described, it will be apparent to those skilled in the art that the same may be varied in many ways without departing from the spirit and scope of the invention. Any and all such modifications are intended to be included within the scope of the appended claims.

What is claimed is:

1. A protective laser beam viewing device comprising:
    A) at least one camera generating video images of a user's environment; said video images including images of laser light at one or more specified wavelengths; and
    B) goggles having at least one video image display receiving the video images from said at least one camera and projecting the images to said at least one video image display in said goggles; said goggles being essentially impermeable to laser radiation and said at least one video image display allowing complete visualization of the path of said laser light at one or more specified wavelengths, whereby said user is able to view his environment, including laser light at one or more specified wavelengths therein, while maintaining ocular protection from said laser light.

2. A protective laser beam viewing device comprising:
A) at least one unshielded camera generating video images of a user's environment; said video images including images of laser light at one or more specified wavelengths; and
B) goggles having at least one video image display receiving the video images from said at least one camera and projecting the images to said at least one video image display in said goggles; said goggles being essentially impermeable to laser radiation,
whereby said user is able to view his environment, including laser light at one or more specified wavelengths therein, while maintaining ocular protection from said laser light.

3. A protective laser beam viewing device to be worn by a user comprising;
A) a pair of laser wavelength band sensitive cameras receiving images of a user's surrounding environment and generating video signals thereof; said laser wavelength band sensitive cameras being capable of imaging one or more wavelengths of laser light; and
B) a pair of goggles receiving the video signals from the pair of laser wavelength band sensitive cameras and transmitting the pair of images individually to a pair of image displays in the goggles, said goggles and said pair of laser wavelength band sensitive cameras to be on the person of said user,
whereby said user is able to view video images of said surrounding environment along with any laser beams of said one or more wavelengths of laser light in said environment,
wherein said device permits the complete visualization of one or more laser beams in said user's environment.

4. A protective laser beam viewing device comprising:
A) a pair of laser wavelength band sensitive unshielded cameras receiving images and generating video signals thereof; and
B) a pair of video image viewing mechanisms receiving the video signals from the pair of laser wavelength band sensitive cameras and transmitting the pair of images individually to a pair of image displays in the video image viewing system.

* * * * *